United States Patent
Draenert et al.

(10) Patent No.: US 6,706,073 B2
(45) Date of Patent: Mar. 16, 2004

(54) NECK-SLIP-PROSTHESIS

(76) Inventors: Klaus Draenert, Gabriel Max Strasse 3, D-181545 Munich (DE); Norbert Walker, Kreuzgarten 29, D-71706 Markgroeningen (DE)

( * ) Notice: Subject to any disclaimer, the term of this patent is extended or adjusted under 35 U.S.C. 154(b) by 0 days.

(21) Appl. No.: 09/919,180

(22) Filed: Jul. 30, 2001

(65) Prior Publication Data

US 2003/0050706 A1 Mar. 13, 2003

(30) Foreign Application Priority Data

Jul. 29, 2000 (DE) .......................... 100 36 985

(51) Int. Cl.[7] .................................................. A61F 2/32
(52) U.S. Cl. .............................. 623/22.46; 623/23.26; 623/23.15
(58) Field of Search ......................... 623/22.11, 22.14, 623/22.4, 22.43, 22.44, 22.45, 22.46, 23.26, 23.12, 23.13, 23.14

(56) References Cited

U.S. PATENT DOCUMENTS

| | | | | |
|---|---|---|---|---|
| 4,080,666 A | * | 3/1978 | Fixel | 623/23.26 |
| 4,129,903 A | * | 12/1978 | Huggler | 623/23.11 |
| 4,795,473 A | * | 1/1989 | Grimes | 623/23.11 |
| 4,976,740 A | * | 12/1990 | Kleiner | 623/23.14 |
| 5,007,935 A | * | 4/1991 | Vincent et al. | 623/23.14 |
| 6,221,074 B1 | * | 4/2001 | Cole et al. | 606/62 |
| 6,383,227 B1 | * | 5/2002 | Baroud et al. | 623/23.22 |

* cited by examiner

*Primary Examiner*—David J. Isabella
(74) *Attorney, Agent, or Firm*—Westman, Champlin & Kelly

(57) ABSTRACT

A hip prosthesis constructed to transfer forces to the femur without relative movements that cause failures. The prosthesis stem has an open sided central bore. The proximal end of the prosthesis is configured to seat against interior surfaces of the femoral canal and support a femur head on a prosthesis shoulder that seats on the stem proximal end while maintaining the neck of the femur intact.

8 Claims, 2 Drawing Sheets

Fig. 1.1

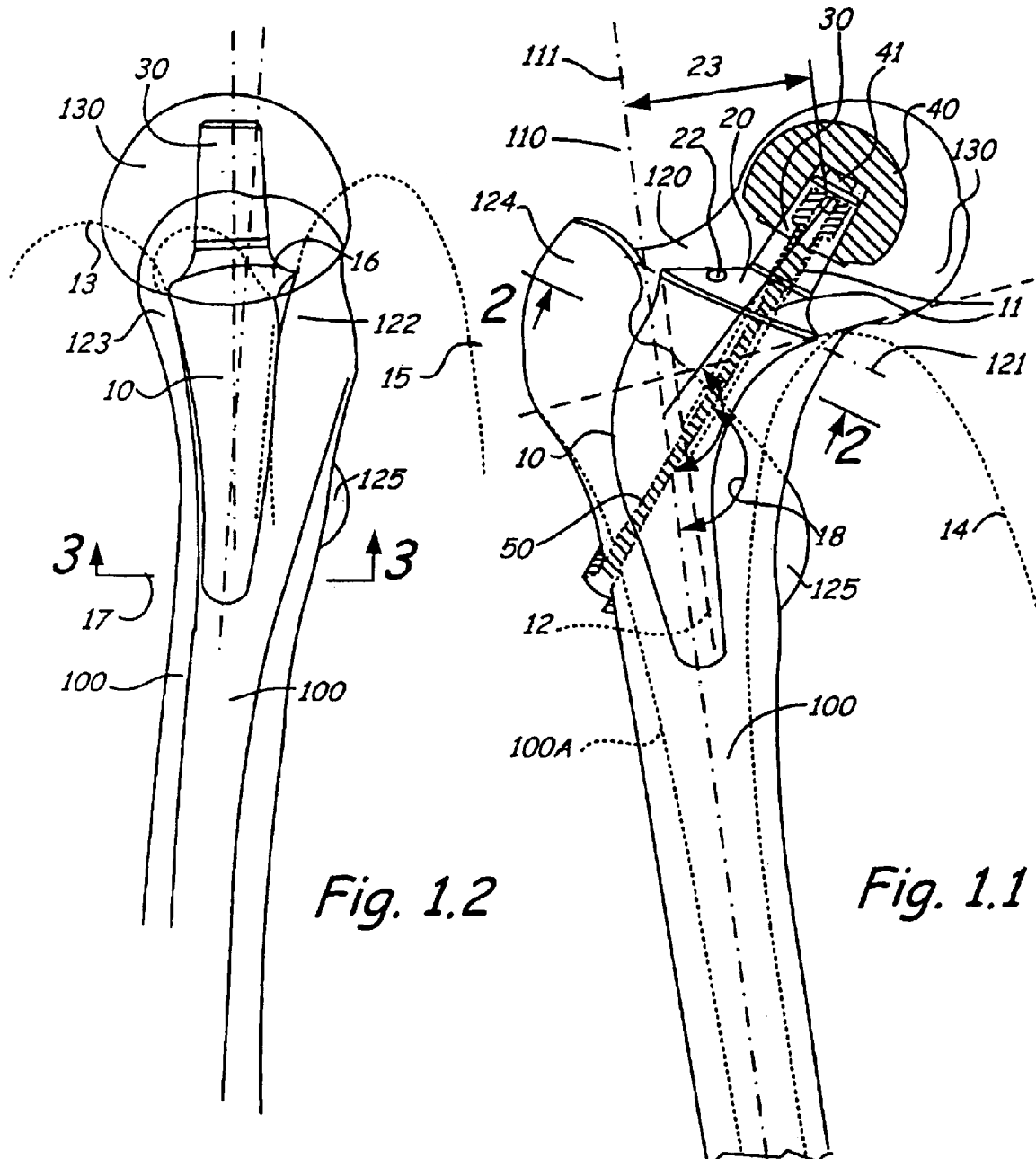
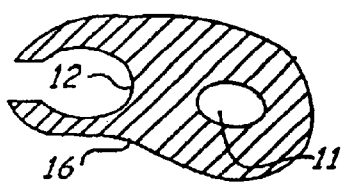
Fig. 2
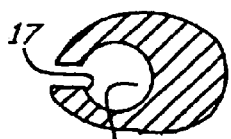
Fig. 3
Fig. 1.2
Fig. 1.1

NECK-SLIP-PROSTHESIS

BACKGROUND OF THE INVENTION

Anatomically, the neck of the femur is the strongest part of the human skeleton. For this reason, it made sense to preserve it in hip joint replacements. This led to various attempts to cap the head of the femur neck. However, this application of force beneath the cap soon resulted in rocking motions of the implant shell, and bone resorption as a result of the relative movement. This ultimately led to fractures of the femoral neck. Based on histopathological research on this approach to anchoring, it was concluded that a sudden change in rigidity between the implant and the bone can only be transferred to the bone in the centrifugal direction by an intramedullary implant.

Accordingly, the object of this invention is to achieve a uniform transfer of force from a rigid implant to the bone.

PRIOR ART

Many attempts have been made to anchor prosthesis stems in the femoral neck. For example, in the case of a thrust-plate prosthesis, Huggler and Jacob attempted—with partial success—to anchor a prosthesis stem component by means of a threaded tensioner extending through the neck. (Huggler, A. H., and Jacob, H. A. C. (1984), The Uncemented Trust Plate Prosthesis. In: Morscher, E. (ed.), *The Cementless Fixation of Hip Endoprostheses*, p. 125, Berlin, Heidelberg, New York: Springer) However, the collar abutments and the rigid design led to bone atrophy and resorption, a clear indication that the transfer of force was not physiological. The problem, moreover, was not remedied by using highly porous structures in the stem element.

The tension anchor prosthesis developed by Nguyen involved a combination of an intramedullary straight-shaft prosthesis and the tension anchor principle. (Gold, T., Schill, S., and Menge, M. (1996), die Zugankerprothses—3 Jahre klinischer Erfahrungen [The Tension Anchor Prosthesis—Three Years of Clinical Experience]. Orthop. Praxis 3:194–197). However, it is precisely the internal structures of the femoral neck that do not allow straight stems or shafts to be anchored; these structures demand right-left opposite symmetry. Histopathological research has now revealed that intramedullary rigid load-bearing members transfer force into the bone structures in a precisely defined manner, a discovery that is exploited in the following invention.

The advantage of a prosthesis limited to transferring the force to the femoral neck is that, in the unlikely event of a failure of the anchorage, it is still possible to employ a normal shaft anchorage without suffering any disadvantages.

SUMMARY OF THE INVENTION

The prosthesis stem of the present invention provides uniform deformation of the neck spongiosa and thus the transfer of force into those bony structures that accept the load from the load-bearing surface of the joint. Force is transferred to the bony structures of the femoral neck and the femur diaphysis without preventing the femur as a whole from deforming. The stem structures are characterized by the so-called U-shape, which is embodied in the femoral neck in dorsal, medial and ventral locations.

The prosthesis thereby has a U-shaped main body, which completely fills the inner surface of the femoral neck and is hollow on the inside.

This completely preserves the anatomical structure of the femoral neck since the osteotomy extends from the lateral transition of the femoral neck to the major trochanter and to the medial head-neck transition; in this way, the internal structures of the femoral neck remain completely intact. The prosthesis contacts the front wall of the femur in an anatomical manner, and its ventral outer surface projects over the bone structures in a parabolic shape.

The axis of the prosthesis corresponds to the femoral axis, as does the lateral open hollow shaft in a parallel position.

BRIEF DESCRIPTION OF THE DRAWINGS

FIG. 1.1 is a frontal view of the neck slip prosthesis of the present invention shown in position on a femur and supporting a femur head;

FIG. 1.2 is an axial view of the non-slip prosthesis shown in FIG. 1;

FIG. 2 is a sectional view taken as on line 2—2 in FIG. 1.1;

FIG. 3 is a sectional view taken as on line 3—3 in FIG. 1.2;

DESCRIPTION OF THE PREFERRED EMBODIMENTS

Figure 4:
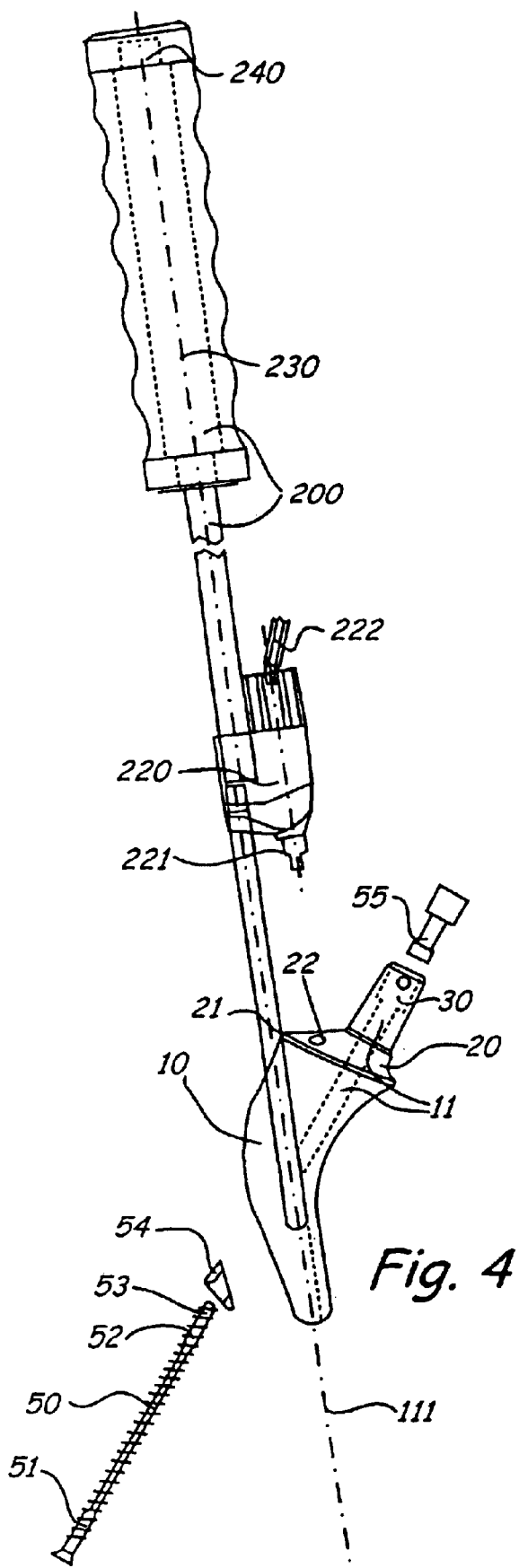
FIG. 4 is a front view of the non-slip prosthesis of the present invention showing an insertion tool.

As shown in FIG. 1.1, the prosthesis comprises a short hollow stem or shaft 10, a shoulder20, and a cone30. The cone 30 has a hole 11 drilled through it axially. The cone 30 can accept various heads, such as shown at 40, for the hip joint. The stem 10 has a deep coaxial dorsal side indentation 16 (FIG. 2) in order to have the stable neck structures on the dorsal side. This gives it a kidney shape when viewed in cross section, as shown in FIG. 2.

The femur bone 100 is shown in the drawings and at an upper end of the greater trochanter 124, which is preserved, and the lesser trochanter 125 are also shown in FIG. 1.1. The osteotomy or cut shown at plane 121 extends from the lateral transition of the femoral neck 120 to the major trochanter 124, thereby preserving the femoral neck intact. The prosthesis contacts the wall 123 of the femoral neck 123 (FIG. 1.2) by fitting the natural contour, and the natural outer surface of the prosthesis projects over the bone structures in a parabolic shape as represented by the line 13. The axis of the prosthesis stem is also indicated at 111, and it corresponds to the femoral axis. The laterally open hollow shaft 112, which is shown in cross section in FIG. 2 and also in FIG. 1.1, so that the axis of the opening having surface 12 and the axis 111 are parallel. FIG. 2 is taken along line 2—2 with closes the femoral canal at an angle, but the view plane of FIG. 2 crosses both the surface 12 and the axis of the femoral canal.

The head of the femur is shown at 130, and it can be seen that when it is in position, the neck 120 of the femur is preserved, and the supporting structure of the greater trochanter and lesser trochanter support the curved upper portions of the prosthesis, such that the stem 10 will fit closely into the femur canal. It should also be noted that the calcar femoris, the rear wall of the femoral neck, is shown at 122 in FIG. 1.2.

The neck-slip prosthesis is inserted axially using a guide instrument 200 shown in FIG. 4. The guide instrument 200 has a handle 230, with an impact member at the end 240, which is convention. The guide instrument has a guide rod 250 that fits into a guide channel 21 along the axis 111 of the stem 10. The medial outer surface of the prosthesis 14, also represented by a dotted line portion 14, to show it is parabolic, compresses the medially adjacent strong spongiosa in the Adam's bow; and likewise, the spongiosa along the wall are uniformly compressed in the dorsal position shown at 16 in FIG. 1.2 as well as in the ventral position along parabolic line 13. The guide instrument 230 is inserted axially along the prosthesis axis 111 and, as shown in FIG. 4, screwed onto the trial prosthesis 21 using the coaxially oriented holding device 220 provided with a threaded screw 221 and a drive socket 222. The screw 221 attaches in to bore 22 when the prosthesis is to be inserted.

A 4.5-mm hole 11 is drilled in the prosthesis through the cone channel after the insertion guide instrument 200 has been removed. Using the outside-in technique, a tension anchor 50 and washer 54 are inserted in hole 11 and the end of anchor 50 is screwed into the cone nut 55. and the tension anchor 150 is then tightened to 2.5 Nm using a torque wrench.

Figure 5:
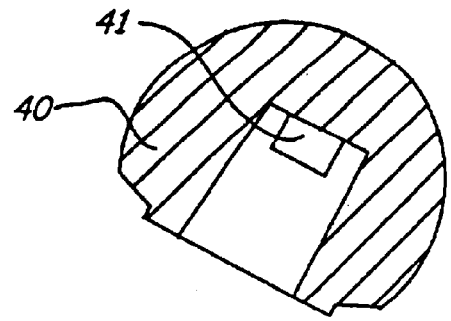
FIG. 5 is a sectional view through a trial ball used with the hip neck slip prosthesis of the present invention.

A trial head 40, shown in FIG. 5, is designed such that after the guide instrument 200 is inserted and the proper position is reached, the nut 55 cannot slide as a result of the nub 41 (FIG. 05/41) that engages the cone.

Example of the Invention

The hip joint is exposed, for example, using Bauer's methodology with the patient in the dorsal position. The dome is removed by an osteotomy along line or plane 121 in FIG. 1.1 and the femur is dislocated. The head of the femur is removed by separation along osteotomy line 121 while preserving the femoral neck 120. The head-end (cone 30) of the prosthesis is prepared. For example, a press-fit ceramic head implant, such as 40, is ground to shape and is inserted in the head or metaphysis 130. The femur is then rotated outward and adducted, and the intermedullary canal of the femur 100 is opened up using an 11.2-mm diamond grinding wheel.

The intermedullary canal is probed using the guide instrument 200, and if this can be done without meeting resistance, the axis 111 of the femoral canal 100A has been correctly established. Then the spongiosa of the metaphysis together with the spongiosa of the femur neck 120 are ground until the trial prosthesis can be inserted into the femoral canal. The U-shape of the prosthesis projects just beyond the inner corticalis of the femoral neck on the ventral side 123 and on the dorsal side 122. The trial prosthesis is then removed, and the corresponding prosthesis is tapped in using the insertion instrument or applicator. Then, using a 4.5 mm bit, a hole for anchor 50 is drilled posterolaterally of the cone to align with hole 11 through the dense portion of the femur, the cone lock nut 55 is inserted in the cone, and the trial head 40 is set to "s"=small. The tension anchor 50 expands along and is centered on the collum-centrum axis of the femur.

The leg (femur) is then repositioned gently and the drilled hole for anchor 50 is located first in the normal zero position, and then in inner rotation and abduction, and the length of the tension anchor through the drilled hole is measured using a gauge. The tension anchor 50 is inserted in cone lock nut 55 and tightened to a torque of 2.5 Nm. The joint is then dislocated, the trial head 40 is replaced with the correct head having the proper length, after the correct head has been definitively identified by trial positioning using the correct trial head.

After repositioning the prosthesis with a definitive ceramic head of the proper length, using the tension anchor in the cone, drainages are inserted and the wound is closed.

Figure 6:
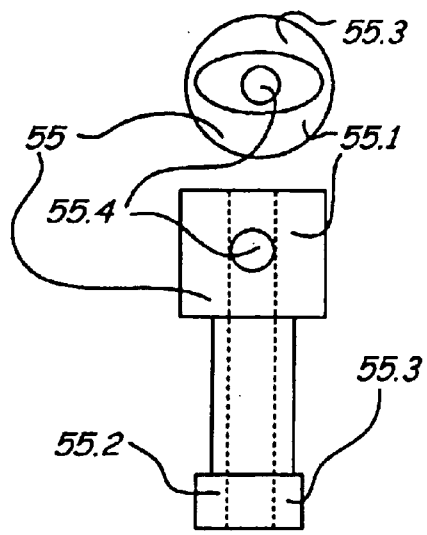
FIG. 6 is an exploded view of a nut used for fastening a cone in the ball of the prosthesis.

In FIG. 6, an exploded view of the cone lock nut 55 is shown. The cone lock nut has cylindrical guides 55.3, as can be seen, and a head or end cap 55.1 shown rotated 90° from its position. As can be seen, the head or end cap has a recess that receives the cone nub 41 so that the nub 41 will retain the nut 55 from rotating. A bore 55.4 goes across the head portion, as well, and there is a central bore also shown at 55.4 in the cover for the nut head. The nut has a central shaft 55.2 between the cylindrical guide members.

Also, in FIG. 4, a washer 54 is illustrated, and the threads on the tension anchor are shown at 52. The head 51 of the tension anchor is also illustrated.

The shoulder 120 and the cone seat on a surface of the proximal end of the stem and as a modular system and can be configured to accept heads of different design, either concentrically with the axis of the cone or eccentrically. The tension anchor 50 is centered on the cone. Additional tension anchors comprising rods, cables or tension wires can be used.

The thrust rod is configured such that the thrust rod is locked at its terminal thread to prevent it from rotating relative to the cone nut, for example by means of one to four HDPE stoppers.

The femoral component is configured such that the femur stem axis 111 coincides with the femur canal axis, and in the frontal plane, the collum-centrum axis of the femur forms an angle of between 125° and 145°, preferably about 135° in the diaphysis axis (CCD angle) 18 as shown in FIG. 1.1. In the axial view, the collum-centrum axis defines an angle between the diaphysis and the femoral neck axis from 5° to 15°, generally in the range of 7°. As shown, the proximal end is configured such that the outer surface of the proximal end is curved on the ventral side in an axially convex shape, or it can be formed in a convex and then a concave shape, and perpendicular thereto it is curved in a concave parabolic shape, such that the center point of surface curvature is on the ventral side and such that the diameter decreases continuously parabolically toward the proximal position.

Further, the medial outer surface of the proximal end of the stem has a convex curvature in the axial position and perpendicular thereto along the medial contour has a concave curvature such that the surface curvature center point is in the medial position, and its radius decreases continuously parabolically in the proximal direction. It also is noted that the one or more of the outer ventral, medial, lateral and dorsal surfaces can be provided with ribs.

The dorsal outer surface of the stem proximal end in the axial position can have a concave or convex-concave-convex shape in the form of a breaking wave or a rounded "3" having asymmetric halves and a rounded transition, and perpendicular thereto, the dorsal outer surface can be straight or concave with a center point of curvature located on the dorsal side. The surface is preferably parabolic so it has a continuous decrease in the radius in the proximal direction.

The stem of the prosthesis makes a transition to the cone by shoulder 20 and the cone, as a modular system, can accept various heads in a concentric or eccentric manner and has the central hole for holding a tension anchor. The implant can have a surface roughness of between 50 and 250 μm, preferably between 70 and 150 μm.

What is claimed is:

1. A femoral component for an artificial hip joint for uncemented implementation characterized by:

a prosthesis comprising a stem having a proximal end, a remote tip end, a dorsal side, a ventral side, a medial side, and a lateral side, the stem having a central axis configured to be substantially coaxial with a femoral canal in which the stem is placed;

the stem having a concave indentation on the dorsal side extending axially from the proximal end toward the tip and engaging the bone structure of a femoral neck at a transition region to a greater trochanter of the femur;

the stem concave indentation being symmetrical right to left from a center;

the proximal end of the stem having a stem section medial side configured to mate with internal structures of the femoral neck of the femur;

a cone for mounting a replacement femur head on the proximal stem section;

the proximal stem section having a support surface for the cone and the stem proximal section joining a lateral stem section that fits into the femoral canal of the femur;

the length of the stem along the central axis being between 4.5 cm and 11 cm; and the stem proximal section having an outer surface configured to contact the inside of the femoral neck dorsally, medially and ventrally through its concave shape.

2. The femoral component of claim 1 wherein the stem has a central bore along the central axis, and the bore being open on a lateral side along at least a portion of the length of the stem.

3. The femoral component of claim 1, and a tension anchor extending through a portion of the femur, through a bore in the proximal end of the stem and engaging the cone to secure the stem to the femur.

4. The femoral component of claim 3, wherein the tension anchor comprises a thrust rod insertable from the lateral side of the femur, and through a bore in the stem to engage the cone, the cone comprising a nut having a thread, and the thrust rod having a head on the exterior of the femur and a thread to mate with the thread in the nut.

5. The femoral component of claim 1, wherein the cone is mounted on a shoulder portion, a stem support surface at the proximal end seating the shoulder portion, and the cone being adapted for supporting a prosthetic head.

6. The femoral component of claim 1, wherein the stem is made from one of the materials in the group consisting of titanium, tantalum, stainless steel or alloys thereof.

7. A femoral component for an artificial hip joint for transferring forces to a femur in which the prosthesis is mounted, the prosthesis comprising:

a stem having a lateral portion and a proximal portion, said lateral portion having a central axis configured to be substantially coaxial with and to fit within a femoral canal in which the stem is placed;

the proximal portion having a surface configuration to seat against interior surfaces of the femur adjacent an osteotomy across the femoral neck and to an extension of the greater and lesser trochanters, the femur neck being left substantially intact when the femur head is removed for insertion of the prosthesis into the femoral canal, the prosthesis stem having a bore with a central axis substantially coinciding in with the axis of the femoral canal, said bore being open to an exterior of the stem along a lateral side thereof such that the stem can flex when inserted in the femoral canal.

8. The femoral component of claim 7, wherein the proximal end has a surface for supporting an attachment cone having a shoulder, the tension anchor extending generally along the collum-centrum axis of the femur, and holding the cone against the proximal end of the prosthesis.

* * * * *